United States Patent [19]

Read

[11] 4,298,569

[45] Nov. 3, 1981

[54] STEAM-FORMALDEHYDE STERILIZATION INDICATOR

[75] Inventor: David M. Read, Harlow, England

[73] Assignee: Minnesota Mining and Manufacturing Company, St. Paul, Minn.

[21] Appl. No.: 115,785

[22] Filed: Jan. 28, 1980

Related U.S. Application Data

[63] Continuation of Ser. No. 881,471, Feb. 27, 1978, abandoned.

[30] Foreign Application Priority Data

Mar. 11, 1977 [GB] United Kingdom ............... 10484/77

[51] Int. Cl.³ ................................................ A61L 2/18
[52] U.S. Cl. ..................................... 422/27; 116/206; 422/36
[58] Field of Search .................... 116/206; 422/56, 57, 422/27, 36; 252/408 R

[56] References Cited

U.S. PATENT DOCUMENTS

| | | | |
|---|---|---|---|
| 2,464,155 | 3/1949 | Russell et al. | 422/57 |
| 2,601,840 | 7/1952 | Smith et al. | 422/56 |
| 2,998,306 | 8/1961 | Huyck et al. | 422/56 |
| 3,238,020 | 3/1966 | Eiseman, Jr. | 422/56 |
| 3,311,084 | 3/1967 | Edenbaum | 116/206 V |
| 3,386,807 | 6/1968 | Edenbaum | 73/356 X |
| 3,409,405 | 11/1968 | Mohan et al. | 23/253 R |
| 3,523,011 | 8/1970 | Bhiwandker et al. | 73/356 X |
| 3,667,916 | 6/1972 | Sliva et al. | 116/206 X |
| 3,684,737 | 8/1972 | Emigh | 73/356 X |
| 3,852,034 | 12/1974 | Gunther | 422/56 |
| 4,015,937 | 4/1977 | Miyamoto | 23/253 R |
| 4,149,852 | 4/1979 | Tiru et al. | 73/356 |

FOREIGN PATENT DOCUMENTS

| | | | |
|---|---|---|---|
| 1104451 | 2/1968 | United Kingdom | 422/56 |
| 1252125 | 11/1971 | United Kingdom | 116/114 V |

OTHER PUBLICATIONS

Publ. Websters New World Dictionary (College Edition) 1957 p. 309.

*Primary Examiner*—Daniel M. Yasich
*Attorney, Agent, or Firm*—Cruzan Alexander; Donald M. Sell; Mark A. Litman

[57] ABSTRACT

Indicators for the steam-formaldehyde sterilization process are provided which undergo a color change when placed in a steam-formaldehyde environment.

5 Claims, No Drawings

STEAM-FORMALDEHYDE STERILIZATION INDICATOR

This is a continuation of application Ser. No. 881,471 filed Feb. 27, 1978, now abandoned.

This invention relates to an indicator designed to undergo a color change when exposed to steam-formaldehyde sterilization.

Steam-formaldehyde sterilization is one well known way of sterilizing items for medical and hospital useage. The process generally involves placing articles to be sterilized in a chamber and then subjecting them to pulses of steam and formaldehyde vapor at sub-atmospheric pressure and relatively low temperatures, for example, of the order of 60° to 80° C. By way of example a steam-formaldehyde sterilization process is described in United Kingdom Patent Specification No. 1,252,125.

It is of course important to know when particular items have been subjected to this steam-formaldehyde sterilization process. Therefore it is an object of the present invention to provide an indicator which can be associated with the articles being sterilized and so subjected to the sterilization conditions and which will give a visual change after this exposure.

According to the invention there is provided an indicator for use in the steam-formaldehyde sterilization process comprising a substrate carrying a dye which will undergo a color change when exposed to formaldehyde vapor in the presence of low temperature steam, the dye being a compound having one or more azo linkages, one or more primary or secondary amino groups, and optionally one or more sulfonic acid groups.

When such a dye is exposed to formaldehyde vapour and steam it undergoes an irreversible change of colour. This irreversibility is essential to ensure that there can be no confusion as to whether a particular item has been subjected to the sterilization process or not. The indicator of the invention is not intended to show that the particular item has been sterilized but merely that it has been exposed to sterilization conditions. Thus, it is still vital for the operator of the sterilization process to follow the correct sterilization procedure, the indicator according to the invention merely indicating that an item has been through the steam-formaldehyde sterilization process.

The indicator should preferably not change colour when subjected to other types of sterilization in common use, e.g. ethylene oxide or high temperature steam, the indicators of the present invention when in the presence of a buffer of a pH greater than about 4 show specificity to low temperature steam-formaldehyde sterilization. Below pH 4 they still react to low temperature steam-formaldehyde sterilization but may also react with ethylene oxide sterilization depending on the precise conditions.

The dye can be present as the free acid or one of its salts.

The dye is preferably a compound containing one or two naphthalene residues. Also there are preferably one or two azo linkages in the compound and one or two primary amino groups.

A particular example of a dye which has been found to give excellent results is that known as Congo red, i.e. 3,3'-[4,4'-bisphenylylene-(azo)] bis [4-amino-1-naphthalene] sulfonic acid or one of its salts such as the disodium salt. The structural formula of this dye is:

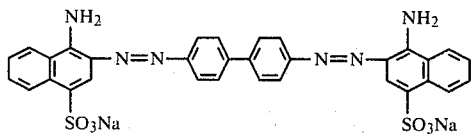

When this dye is subjected to formaldehyde vapours at a temperature of 70° C. its initial red colour is irreversibly changed to yellow. The visual change from red to yellow is very marked. It is desirable to include a buffer in the indicator to stabilize the dye until it is exposed to the sterilizing conditions. In addition the presence of a buffer appears to make the colour change of the dye largely independent of the concentration of formaldehyde; this is particularly important when relatively low concentrations of formaldehyde are used. Thus under alkaline conditions Congo red is less sensitive to formaldehyde than under acid conditions.

Examples of other dyes which can be used are Naphthalene Black 10B, i.e.:

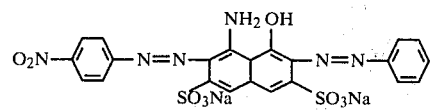

and Benzo purpurin. When Naphthalene Black 10B is reacted with formaldehyde its colour changes from blue to green and when Benzo purpurin is reacted with formaldehyde its colour changes from deep red to light pink.

As noted above it is desirable to include a buffer in the indicator. When the dye Congo red is used it is preferred to use a buffer with a pH of from 4 to 6 although the colour change also occurs at neutral and alkaline pH, the most preferred pH being about 5, since at that pH relatively low formaldehyde vapour concentrations bring about the desired colour change and at this pH there is no colour change when the indicator is subjected to ethylene oxide sterilization conditions.

The buffer used is preferably a self buffering compound but this is not essential. Examples of suitable buffers and buffering compositions are potassium hydrogen phthalate, potassium dihydrogen citrate, a mixture of trisodium citrate and citric acid, and sodium hydrogen tartrate, but other buffers or buffering compositions which do not react with the dye and which will buffer the dye to the desired pH range can be used.

In addition to the dye which changes colour under the steam-formaldehyde sterilizing conditions, the indicator may contain one or more additional dyes which do not change colour during the sterilization. This additional dye is, however, chosen to enhance the colour change of the indicator. For example a blue dye such as Irgacet Blue 2 GLN or Methylene Blue, can be combined with Congo red to give an indicator whose initial colour is magenta which changes to green upon exposure to the sterilization conditions. By the use of one or more additional dyes in this way, one can choose the desired initial and final colours of the indicator and this may be advantageous both to distinguish the indicator of the present invention from indicators used for other types of sterilization and to give a marked color change.

The substrate of the indicator could be a piece of porous material such as porous filter paper, in which case the paper can be impregnated with a solution of the dye and allowed to dry. The concentration of the dye solution can vary widely, for example, from 23 g/l to 1.6 g/l. although the best colour change appears to be given if the concentration of the dye solution is from 4 to 8 g/l.

Preferably however, the dye is incorporated into an ink composition which is printed onto a substrate. This ink composition can contain conventional ink additives such as a binder. The ink composition can be an aqueous ink with the dye dissolved or dispersed in water or can be a non-aqueous system containing the dye dispersed or dissolved in an organic solvent or organic solvents and water emulsion together with other additives such as waxes, gums, polymers, methyl or ethyl cellulose and carboxymethyl cellulose to thicken the ink.

The dye can also be incorporated into a coating which is brushed or coated by a coating knife on the substrate or a substrate can be dipped into a composition containing the dye.

The substrate is preferably in the form of a strip of material which carries on its other face a pressure-sensitive adhesive. Examples of such material are a paper base (e.g., masking tape) or a strip of synthetic plastics material.

A preferred indicator according to the invention comprises a strip of material which carries on one face a dried ink composition containing the dye and which also has a pressure-sensitive adhesive layer and optionally other layers. In this way the operator of a sterilization process can be provided with a roll of this strip and can attach short lengths torn from the roll to each item to be subjected to sterilization. Suitable pressure-sensitive adhesives and release sheets or coatings to be associated therewith are very well know and need no further comment.

The brightness of the ink containing the dye can be increased by incorporating brighteners into the ink and one example is gelatin. This latter compound can also have some binding action and other polymeric materials may also or alternatively be incorporated to assist in binding and stabilizing the indicator until use and examples are polyvinyl alcohol and polyvinyl pyrrolidone. Polyvinyl alcohol is particularly preferred when the dye is Congo red with which it forms a molecular complex which appears to aid dispersion and stabilize the red color of the dye.

Preferably, the dye is printed, coated or impregnated on to the substrate in the form of a characteristic pattern, e.g., repeating strips or bars extending across the width of the strip. Such patterns are well known with the indicators for other types of sterilization processes.

The invention will now be illustrated with reference to the following Examples and the accompanying drawing.

EXAMPLE 1

A piece of pressure-sensitive masking tape 10 commercially available under the trade name "Scotch" was printed on the face not carrying the pressure-sensitive adhesive with substantially transverse bars 12 of an ink composition, the printed pattern being as shown in the accompanying drawing. The red inked bars 12 of the tape were then dried.

The ink composition used was prepared as follows:

(1) 18 g of gelatin were dissolved in 300 ml water at a temperature of 60° C.;
(2) 100 g polyvinyl alcohol were dissolved in 600 ml water at 80° C.;
(3) 15 g Congo red were dissolved in a mixture of 200 ml of water and 200 ml of isopropyl alcohol; and
(4) the gelatin and polyvinyl alcohol solutions were added to the Congo red solution with stirring.

Portions of the resulting indicator tape were tested and the inked bars found to change from their red color to a yellow color when exposed to formaldehyde vapor in the presence of steam.

Other portions of the tape were subjected to a conventional steam-formaldehyde sterilization of approximately 2 hours in a hospital steam-formaldehyde sterilization apparatus of 140 liters internal volume. During this time 5 pulses of formaldehyde solution were introduced giving a total volume of 250 ml of formaldehyde solution, corresponding to a peak concentration of about 143 mg of formaldehyde per liter of internal volume of apparatus. During sterilization the temperature was kept at 60° to 70° C. After completion of the sterilization the portions of indicator tape were recovered and the red printed bars found to have changed to yellow. The change in color could be very clearly seen.

When further portions of the indicator tape were subjected to an ethylene oxide sterilization in a Victoria Mark II instrument for one hour at approximately 55° C., they were recovered at the end of the sterilization and it was found that the inked portions had not changed color.

Similarly, when further portions of the indicator tape were subjected to a steam autoclave sterilization in the absence of formaldehyde during which the temperature was maintained at 134° C. for 3½ minutes, the indicator tape portions were recovered and found to be of an unchanged color.

EXAMPLE 2

An aqueous solution containing 5.3 g of Congo red per liter of solution was prepared and to this was added per liter of Congo red solution, 100 ml of a 5% Methylene Blue solution in water. A filter paper was dipped in this solution and allowed to air dry. The paper was then dipped in a solution of potassium hydrogen phthalate in water, the concentration of the potassium hydrogen phthalate solution being 5%, although a concentration in the range of from 2.5% to 10% can be used.

Once the resulting paper had been allowed to dry it was of a magenta color.

Portions of this resulting paper were subjected to conventional steam-formaldehyde sterilization in a commercially available steam-formaldehyde sterilization apparatus which had an internal volume of 425 liters and whose steam-formaldehyde sterilization cycles included 6 pulses of 50 ml of a 37% formaldehyde solution over a period of 30 minutes at 73° C., corresponding to a peak concentration of about 45 mg of formaldehyde per liter of internal volume of the apparatus. After completion of the sterilization the portions of filter paper was recovered and found to have changed to a green color.

I claim:

1. A method for indicating that an article has undergone steam-formaldehyde sterilization which comprises attaching an indicator to an article, said indicator comprising a substrate carrying a dye which will undergo an irreversible color change when exposed to formaldehyde vapor in the presence of low temperature steam and wherein a buffering agent is mixed with said dye and said buffer has a pH of from 4 to 6, and then inserting said article with indicator into an environment wherein the article and indicator are exposed to steam and formaldehyde so that the article is sterilized wherein said steam is between 60° and 80° C. and where said indicator will not change color when exposed to 134° C. steam in the absence of formaldehyde for 3½ minutes.

2. The method of claim 1 wherein said dye and buffering agent are mixed in a binder.

3. The method of claim 1 or 2 wherein said dye comprises 3,3'-[4,4'-bisphenylylene-(azo)] bis [4-amino-1-naphthalene].

4. The method of claim 1 or 2 wherein said dye comprises Congo Red.

5. A method for indicating that an article has undergone steam-formaldehyde sterilization which comprises attaching the indicator of claim 1 to an article which requires sterilization and inserting said article with indicator into a steam-formaldehyde sterilization chamber.

* * * * *